US008648184B2

(12) United States Patent
Lee et al.

(10) Patent No.: US 8,648,184 B2
(45) Date of Patent: Feb. 11, 2014

(54) RECOMBINANT VECTORS CARRYING ZEARALENONE-INDUCIBLE PROMOTER AND METHODS FOR PRODUCING PROTEINS AND DETECTING ZEARALENONE USING THEM

(75) Inventors: Yin Won Lee, Seoul (KR); Jung Kwan Lee, Seoul (KR); Ae Ran Park, Gwangju (KR); Seung Hoon Lee, Incheon (KR); Ho Kyung Son, Seoul (KR)

(73) Assignee: SNU R&DB Foundation (KR)

( * ) Notice: Subject to any disclaimer, the term of this patent is extended or adjusted under 35 U.S.C. 154(b) by 436 days.

(21) Appl. No.: 12/966,696

(22) Filed: Dec. 13, 2010

(65) Prior Publication Data

US 2011/0154540 A1 Jun. 23, 2011

(30) Foreign Application Priority Data

Dec. 14, 2009 (KR) ........................ 10-2009-0123711

(51) Int. Cl.
| | |
|---|---|
| *C07H 21/04* | (2006.01) |
| *A01H 9/00* | (2006.01) |
| *C12N 15/82* | (2006.01) |
| *C12N 15/00* | (2006.01) |
| *C12Q 1/02* | (2006.01) |
| *C12N 1/00* | (2006.01) |
| *C12N 1/20* | (2006.01) |
| *C12P 21/06* | (2006.01) |

(52) U.S. Cl.
USPC ............ 536/24.1; 800/295; 435/468; 435/49; 435/320.1; 435/29; 435/243; 435/252.3; 435/69.1

(58) Field of Classification Search
None
See application file for complete search history.

(56) References Cited

PUBLICATIONS

Komarnytsky & Borisjuk, Genetic Engin 25:113-41 (2003).*
Dolferus et al., Plant Phys 105:1075-87 (1994).*
Kim et al. Plant Mol Biol 24:105-17 (1994).*
Donald & Cashmore, EMBO J 9(6):1717-26 (1990).*
Lee et al., Appl Environ Microbiol 76:3089-96 (2010).*
Jamal et al., Biotech Adv 27:914-23 (2009).*
Willyerd et al. (Appl Environ Microbiol 75:5417-20 (2009).*
Lysoe et al., App Environ Microbiol 72(6):3924-32 (2006).*
Fleissner et al., Mol Plant Microber Interact 15(2):102-08 (2002).*
A.E. Desjardins, "Fusarium mycotoxins: chemistry, genetics and biology," APS Press, 2006, St. Paul, MN.
B. Horwitz et al., "A G protein Alpha Subunit from *Cochliobolus heterostrophus* involved in Mating and Appressorium Formation," Fungal Genetics and Biology, 1999, pp. 19-32, vol. 26.
B. Romero et al., "The *Aspergillus nidulans* alcA promoter drives tightly regulated conditional gene expression in *Aspergillus fumigatus* permitting validation of essential genes in this human pathogen," Fungal Genet and Biology, 2003, pp. 103-114, vol. 40.

(Continued)

*Primary Examiner* — Anne Marie Grunberg
*Assistant Examiner* — Russell Boggs
(74) *Attorney, Agent, or Firm* — Hershkovitz & Associates, PLLC; Abe Hershkovitz

(57) ABSTRACT

The present invention relates to a zearalenone-inducible promoter originated from *Gibberella zeae*, recombinant vectors comprising the promoters, methods of producing proteins and detecting plants contaminated with zearalenone. The promoter of the present invention can be used for studying essential genes in fungus, characterizing the mechanism of self/nonself recognition in *G. zeae*, engineering of plant systems to generate plants that can recognize a *G. zeae* attack and detecting ZEA contamination as a biosensor.

20 Claims, 5 Drawing Sheets

(56) References Cited

PUBLICATIONS

C. Bacon et al., "Media for Indentification of *Gibberella zeae* and Production of F-2-(Zearalenone)," Applied and Environmental Microbiology, 1977, pp. 445-449, vol. 33, No. 2.

C. J. Mirocha et al., "Oestrogenic mycotoxins synthesized by *Fusarium*," sp., In I. F. H. Purchase (ed.), Mycotoxins. Elsevier Scientific Publishing, 1974, pp. 129-148 Amsterdam, Netherlands.

C. Micali et al., "A Nonself Recognition Gene Complex in *Neurospora crassa*," Genetics, 2006, pp. 1991-2004, vol. 173.

D. Chevanne et al., "Identification of the het-r vegetative incompatibility gene of *Podospora anserina* as a member of the fast evolving HNWD gene family," Curr Genet, 2009, pp. 93-102, vol. 55.

D. Gebhart et al., "Identification of a Copper-Inducible Promoter for use in Ectopic Expression in the Fungal Pathogen *Histoplasma capsulatum*," Eukaryotic Cell, 2006, pp. 935-944, vol. 5, No. 6.

D. P. Yevtushenko et al., "Wound-inducible promoter from poplar is responsive to fungal infection in transgenic potato," Plant Science, 2004, pp. 715-724, vol. 167.

E. Lysoe et al., "Real-Time Quantitative Expression Studies of the Zearalenone Biosynthetic Gene Cluster in *Fusarium graminearum*," Phytopathology 2009, pp. 176-184, vol. 99, No. 2.

E. Lysoe et al., "The PKS4 Gene of *Fusarium graminearum* Is Essential for Zearalenone Production," Applied Environmental Microbiology, 2006, pp. 3924-3932, vol. 72, No. 6.

F. Eckstein, "Oligonucleotide Synthesis: A Practical Approach," IRL Press, 1991.

G. G. Meynell et al., "Theory and Practice in Experimental Bacteriology," $2^{nd}$ ed. Cambridge: Cambridge University Press, 1970.

G. M. Blackburn et al., "Nucleic Acids in Chemistry and Biology," Oxford University Press, 2006.

G. P. Munson et al., "Identification of a Copper-Responsive Two-Component System on the Chromosome of *Escherichia coli* K-12," Journal of Bacteriology, 2000, pp. 5864-5871, vol. 182, No. 20.

G. T. Hermanson, "Bioconjugate Techniques," Academic Press, 1996.

H. E. Kubitschek, "Introduction to Research with Continuous Cultures," Prentice-Hall, Inc., Englewood Cliffs N.J., 1970.

H-Y. Yu et al., "Functional analyses of heterotrimeric G protein Gα and Gβ subunits in *Gibberella zeae*," Microbiology, 2008, pp. 392-401, vol. 154.

J-H. Yu et al., "Double-joint PCR: a PCR-based molecular tool for gene manipulations in filamentous fungi," Fungal Genetics and Biology, 2004, pp. 973-981, vol. 41.

I. Gaffoor et al., "Characterization of Two Polyketide Synthase Genes Involved in Zearalenone Biosynthesis in *Gibberella zeae*," Applied Environmental Microbiology, 2006, pp. 1793-1799, vol. 72, No. 3.

J. E. Jurgenson et al., "A Genetic Map of *Gibberella zeae (Fusarium graminearum)*," Genetics, 2002, pp. 1451-1460, vol. 160.

J. F. Leslie, "Fungal Vegetative Compatibility," Annu. Rev. Phytopathol, 1993, pp. 127-150 vol. 31.

J. F. Leslie et al., "The *Fusarium* laboratory manual. Blackwell Professional," Ames, IA, 2006.

J. Kim, "GIP2, a Putative Transcription Factor That Regulates the Aurofusarin Biosynthetic Gene Cluster in *Gibberella zeae*," Applied and Environmental Microbiology, 2006, pp. 1645-1652, vol. 72, No. 2.

J. Lee et al., "Alignment of Genetic and Physical Maps of *Gibberella zeae*," Applied and Environmental Microbiology, 2008, pp. 2349-2359, vol. 74, No. 8.

J. Lee et al., "Expression and Function of Sex Pheromones and Receptors in the Homothallic Ascomycete *Gibberella zeae*," Eukaryotic Cell, 2008, pp. 1211-1221, vol. 7, No. 7.

J. Mandelstam et al., "Biochemistry of Bacterial Growth," $3^{rd}$ ed. Oxford: Blackwell, 1982.

J. N. Park et al., "Identification of the Cadmium-Inducible Hansenula polymorpha SEO1 Gene Promoter by Transcriptome Analysis and Its Application to Whole-Cell Heavy-Metal Detection Systems," Applied and Environmental Microbiology, 2007, pp. 5990-6000, vol. 73, No. 19.

J. Zuo et al., "Chemical-inducible systems for regulated expression of plant genes," Methods Mol. Biol., 2006, pp. 329-342, vol. 323.

J. S. Sambrook et al., "A Laboratory Manual, Cold Spring Harbor Laboratory Press," Molecular Cloning, 2001.

J-Y. Shoji et al., "Development of *Aspergillus oryzae* thiA" promoter as a tool for molecular biological studies, FEMS Microbiology Letters, 2005, pp. 41-46, vol. 244.

K. Seong et al., "Random Insertional Mutagenesis Identifies Genes Associated with Virulence in the Wheat Scab Fungus *Fusaruim graminearum*," Phytopathology, 2005, pp. 744-750, vol. 95.

K. Willyerd et al., "Controlled Gene Expression in the Plant Pathogen *Cryphonectria parasitica* by Use of a Copper-Responsive Element," Applied Environmental Microbiology,2009, pp. 5417-5420, vol. 75, No. 16.

M. J. Gait, "Oliginucleotide Synthesis: A Practical Approach," IRL Press, 1985.

M. J. Gait, "Oliginucleotide and Analogues: A Practical Approach," IRL Press, 1990.

M. Osusky et al., "Transgenic plants expressing cationic peptide chimeras exhibit broad-spectrum resistance to phytopathogens," Nature Biotechnology, 2000, pp. 1162-1166, vol. 18.

N. Verma et al., "Biosensors for heavy metals," BioMetals, 2005, pp. 121-129, vol. 18.

P. Gerhardts "Manual of Methods for General bacteriology," Washington: Am. Soc. Microbiol, 1981.

R. B. Waring et al., "Characterization of an inducible expression system in *Aspergillus nidulans* using alcA and tubulin-coding genes," Gene, 1989, pp. 119-130, vol. 79.

R. H. Proctor et al., "Reduced Virulence of *Gibberella zeae* Caused by Disruption of a Trichothecene Toxin Biosynthetic Gene," MPMI, 1995, pp. 593-601, vol. 8, No. 4.

R. L. Adams et al., "The Biochemistry of the Nucleic Acids," Chapman & Hall, 1992.

R. L. Mark et al., "Regulation of gene expression in industrial fungi: *Trichoderma*," Appl. Microbiol. Biotechnol. 2003, pp. 515-522, vol. 60.

R. W. Skadsen et al., "Cloning of the promoter for a novel barley gene, Lem1, and its organ-specific promotion of *Gfp* expression in lemma and palea," Plant Molecular Biology, 2002, pp. 545-555, vol. 49.

S. Harris, "Morphogenesis in germinating *Fusarium graminearum* macroconidia," Mycologia,2005, pp. 880-887, vol. 97, No. 4.

S. Tada et al., "Construction of a fusion gene comprising the Taka-amylase A promoter and the *Escherichia coli* β-glucuronidase gene and analysis of its expression in *Aspergillus oryzae*," Mol Gen Genet, 1991, pp. 301-306, vol. 229.

T. Lee et al., "Tri13 and Tri7 Determine Deoxynivalenol- and Nivalenol-Producing Chemotypes of *Gibberella zeae*," Applied and Environmental Microbiology, 2002, pp. 2148-2154, vol. 68, No. 5.

Y. Han et al., "Functional analysis of the homoserine O-acetyltransferase gene and its identification as a selectable marker in *Gibberella zeae*," Curr Genet. 2004, pp. 205-212, vol. 46.

Y. Kim et al., "Two different polyketide synthase genes are required for synthesis of zearalenone in *Gibberella zeae*," Molecular Microbiology, 2005, pp. 1102-1113, vol. 58, No. 4.

Z. Hou et al., "A Mitogen-Activated Protein Kinase Gene (MGV1) in *Fusarium graminearum* Is Required for Female Fertility, Heterokaryon Formation, and Plant Infection," MPMI, 2002, pp. 1119-1127, vol. 15, No. 11.

Z. Shabarova et al., "Advanced Organic Chemistry of Nucleic Acids," Weinheim, 1994.

\* cited by examiner

RECOMBINANT VECTORS CARRYING ZEARALENONE-INDUCIBLE PROMOTER AND METHODS FOR PRODUCING PROTEINS AND DETECTING ZEARALENONE USING THEM

BACKGROUND OF THE INVENTION

1. Field of the Invention

The present invention relates to a zearalenone-inducible promoter originated from *Gibberella zeae*, recombinant vectors comprising the promoters, methods of producing proteins and detecting plants contaminated with zearalenone.

2. Description of the Related Art

The ascomycete fungus *Gibberella zeae* (anamorph: *Fusarium graminearum*) is an important plant pathogen that causes fusarium ear rot disease on maize and head blight on barley, wheat, and rice (17). This fungus produces mycotoxins, such as trichothecenes and zearalenone (ZEA), which are harmful to humans and animals. Trichothecenes are sesquiterpenoids that are potent inhibitors of eukaryotic protein biosynthesis and cause food refusal, diarrhea, emesis, alimentary hemorrhaging, and contact dermatitis in animals (3). In addition, trichothecenes are virulence factors in plants (26).

ZEA [6-(10-hydroxy-6-oxo-trans-1-undecenyl)-β-resorcyclic acid lactone] is a polyketide metabolite (3) that causes estrogenic disorders in laboratory rats, mice, and farm-raised swine that have ingested fusarium-contaminated maize, wheat, and barley (22). ZEA biosynthesis genes in *G. zeae* are located in a gene cluster that contains two polyketide synthase genes, one putative transcription factor, and one putative isoamyl alcohol oxidase gene (4, 12, 19). ZEA-nonproducing mutants generated from *G. zeae* field strains do not have any noticeable phenotypic changes except for a loss of ZEA production (4, 12, 19). The biological functions of ZEA in *G. zeae* have not been characterized to date.

Molecular studies of G. zeae have been widely performed by many research groups since the genome was sequenced by the Broad Institute of Cambridge, Mass. Molecular manipulations, including targeted gene deletion, gene overexpression, and gene fusion to green fluorescent protein (GFP), are relatively easy to perform with this fungus. In addition, mutant collections of *G. zeae* generated through restriction enzyme-mediated integration mutagenesis are currently available (6, 29), and the functions of genes related to toxin biosynthesis, sexual reproduction, pigmentation, and virulence in the fungus have been well characterized (3, 9, 11, 14, 37). However, a conditional expression system that uses a conditional promoter for the study of essential genes and induction of transgenes is currently not available in *G. zeae*.

Regulation of gene expression by conditional promoters, including copper-, cadmium-, thiamine-, and alcohol-responsive promoters, has been developed in various organisms (23, 25, 30, 34-35). These systems have been used as tools for studying the molecular regulation of target gene expression and protein production of genes in industrial fungi (20, 39). Further, recombinant bacterial and fungal strains that possess a metal-inducible promoter have been used as biosensors for monitoring heavy metal contamination (25, 33). A woundinducible promoter was also recently used to generate transgenic plants that can recognize fungal infections (36).

Previously, the present inventors performed a microarray analysis to characterize the biological functions of ZEA in *G. zeae* and found that the transcripts of certain genes, including ZEA biosynthetic genes, were highly elevated after ZEA treatment. The present inventors hypothesized that the promoters of genes upregulated by ZEA treatment could be used as inducible promoters for the conditional expression of target genes in response to ZEA treatment. From our analysis of genes upregulated by exogenous treatment of ZEA, one ZEA response gene (Broad Institute; FGSG_04581.3) was selected for further study based on an expression level that was 50 times higher than that of the control in cultures containing ZEA. The gene was designated a ZEA response gene (ZEAR). The present inventors have successfully identified a ZEA-inducible promoter and applied it as a tool for regulating gene expression in *G. zeae*.

SUMMARY OF THE INVENTION

The present inventors have made intensive researches to develop efficient methods of detecting a plant contaminated with zearalenone (ZEA). As a result, we have found that a gene is highly upregulated by exogenous treatment of ZEA and successfully identified a ZEA-inducible promoter.

Accordingly, it is an object of this invention to provide a zearalenone-inducible promoter.

It is another object of this invention to provide a recombinant vector comprising a zearalenone-inducible promoter.

It is still another object of this invention to provide a recombinant microorganism transformed with a recombinant vector comprising a zearalenone-inducible promoter.

It is further object of this invention to provide a plant transformed with a recombinant vector comprising a zearalenone-inducible promoter.

It is still further object of this invention to provide a method of producing a target protein by a recombinant microorganism transformed with a recombinant vector comprising a zearalenone-inducible promoter.

It is another object of this invention to provide a method of detecting a plant contaminated with zearalenone.

It is still another object of this invention to provide a kit for detecting a plant contaminated with zearalenone.

Other objects and advantages of the present invention will become apparent from the following detailed description together with the appended claims and drawings.

DETAILED DESCRIPTION OF THIS INVENTION

Figure 1:
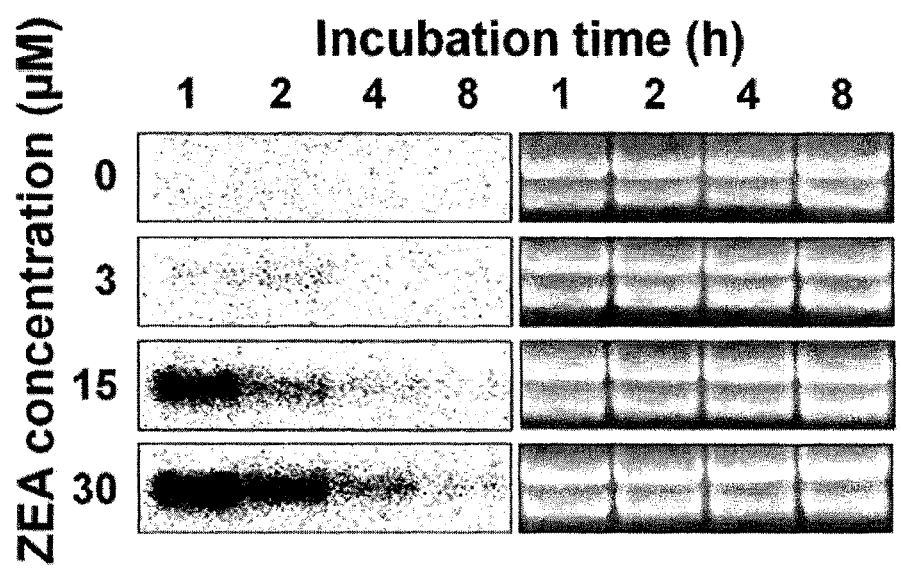
FIG. 1 is a photograph showing the results of analysis of ZEAR mRNA expression level. Total RNA of the wild-type strain GZ03639 of *G. zeae* was extracted from CM cultures grown for 1, 2, 4, and 8 h after ZEA treatment. Twenty micrograms was subjected to Northern analysis, with the PCR product of ZEAR, amplified from GZ03639 with zear-orf1/zear-orf2 primers, serving as a probe. An ethidium-bromide-stained gel is shown as a loading control.
Figure 2:
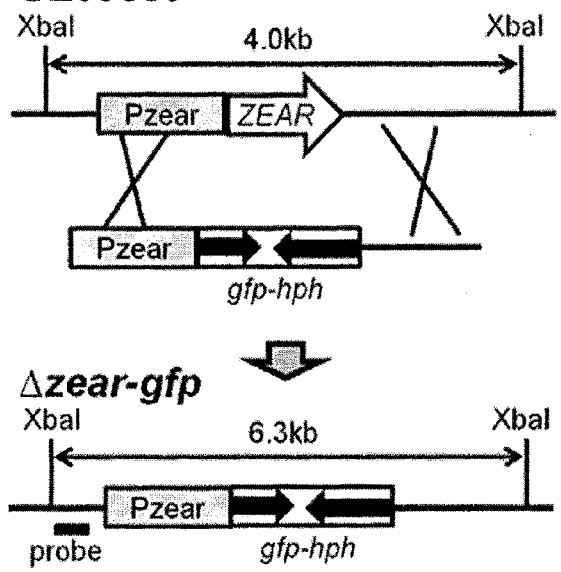
FIG. 2 schematically represents the strategy for targeted gene fusion with GFP. The promoter and terminator regions of ZEAR were fused with gfp::hph to generate the Δzear-gfp mutant, where GFP expression was controlled by the promoter of ZEAR. In the Southern blot, lane 1 is GZ03639, lanes 2 and 3 are mutants that carry multiple integration events, and lanes 4 and 5 are positive mutants where the target gene was replaced with Pzear::gfp::hph.
Figure 2:
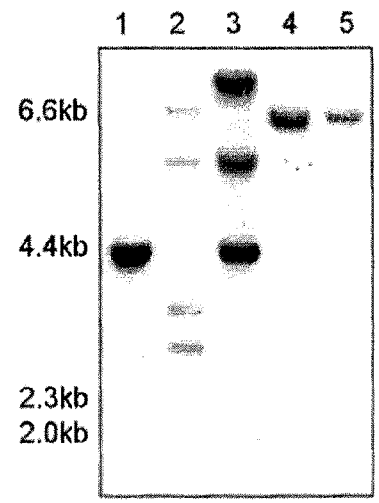
Figure 3:
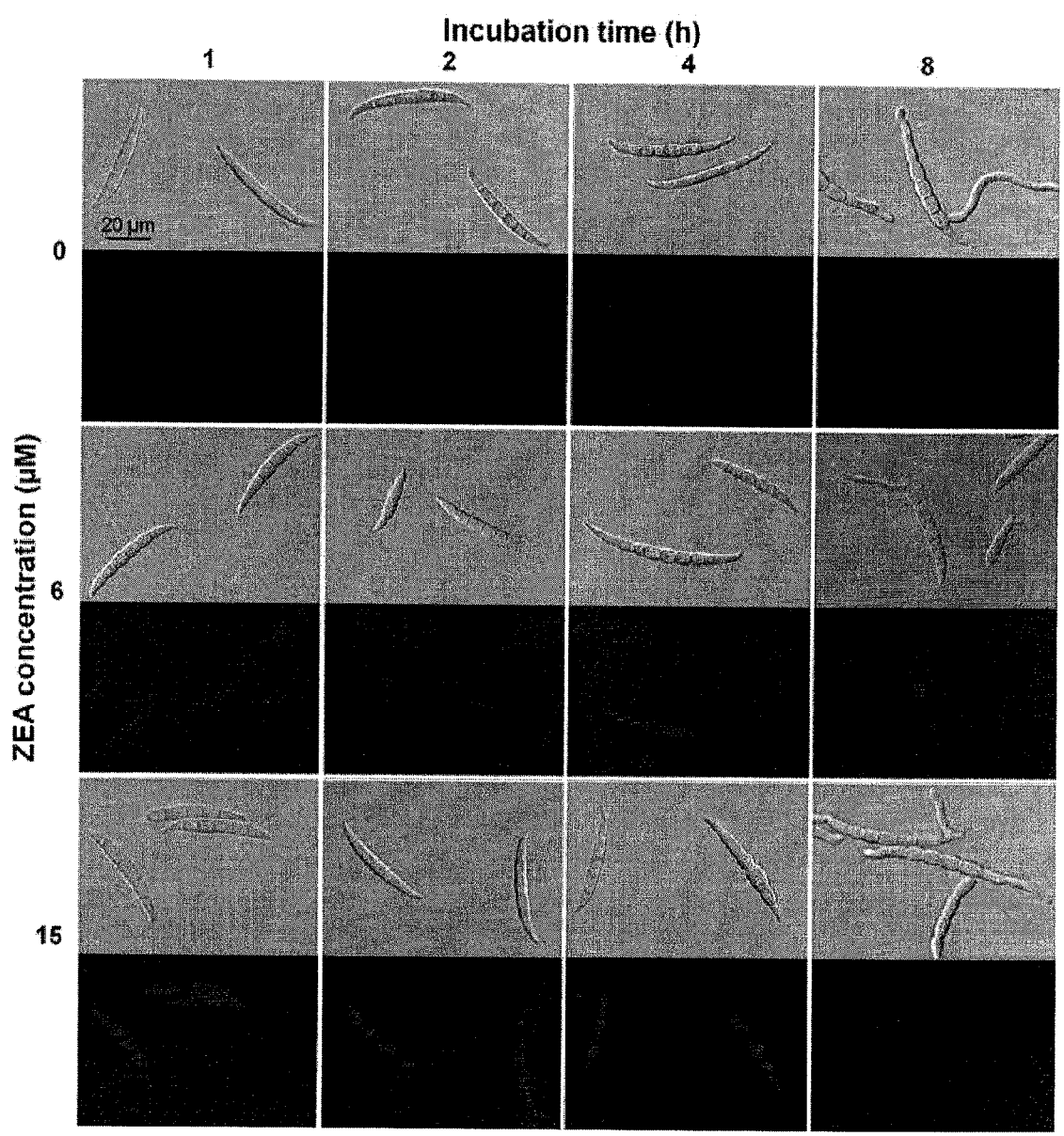
FIG. 3 is a photograph showing the results of GFP expression of the Δzear-gfp mutant. Conidia were incubated for 1, 2, 4, and 8 h in CMsupplemented with ZEA. First, third, and fifth lines, bright-field microscopy; second, fourth, and sixth lines, fluorescence microscopy.
Figure 4:
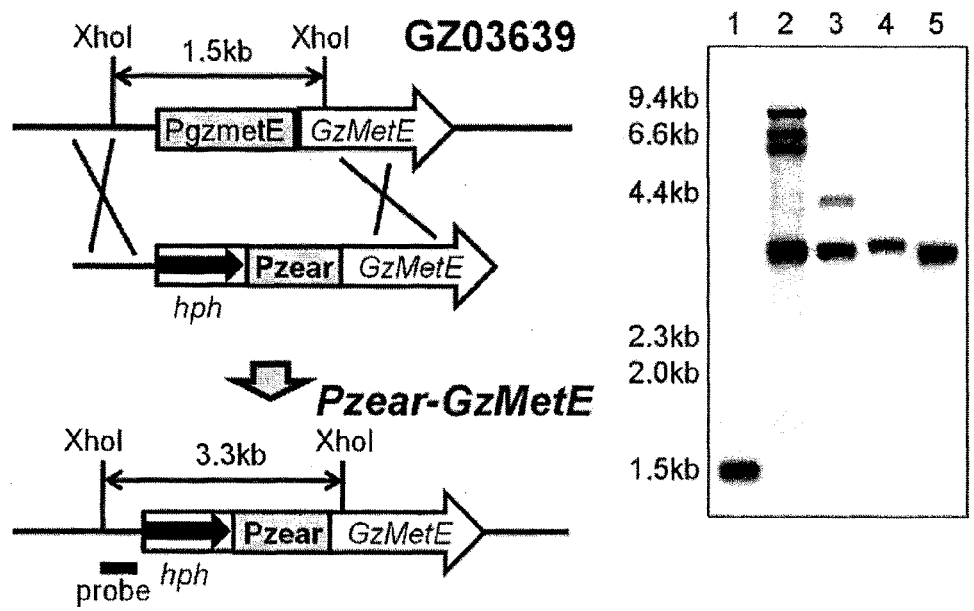
FIG. 4 schematically represents the strategy for promoter replacement. The GzmetE promoter (PgzmetE) was replaced with the zearalenone-inducible promoter, Pzear. In the Southern blot, lane 1 is GZ03639, lanes 2 and 3 are mutants that carry multiple integration events, and lanes 4 and 5 are positive mutants that carry the Pzear promoter.
Figure 5:
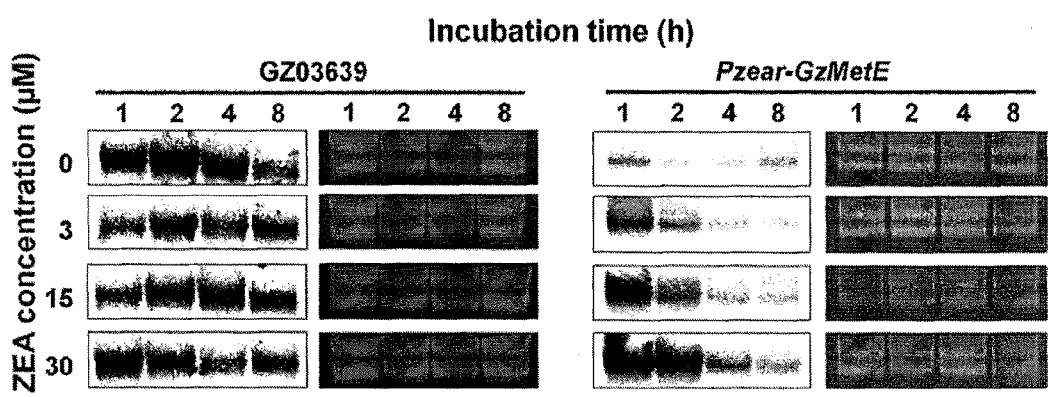
FIG. 5 is a photograph showing the results of analysis of GzmetE mRNA expression. Total RNAs from wild-type strain GZ03639 of *G. zeae* and the Pzear-GzmetE mutant were extracted from MM cultures grown for 1, 2, 4, and 8 h after ZEA treatment. Twenty micrograms was subjected to Northern blot analysis, with the PCR product of GzmetE, amplified from GZ03639 with gzmetE-orf1/gzmetE-orf2 primers, serving as a probe. An ethidiumbromide-stained gel is shown as a loading control.
Figure 6:
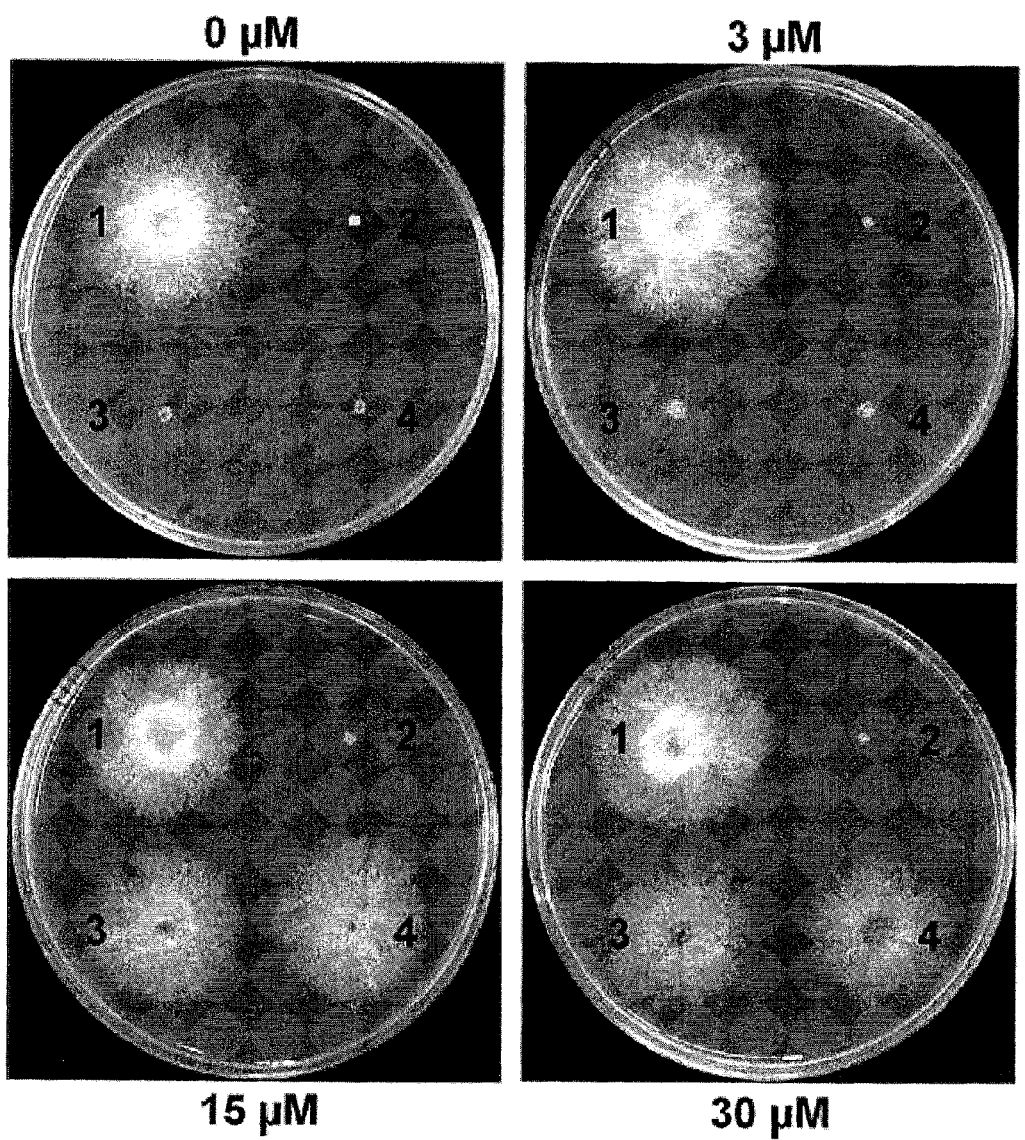
FIG. 6 represents mycelial growth of the strains on MM supplemented with ZEA. Spot 1, GZ03639; spot 2, ΔgzmetE; spots 3 and 4, Pzear-GzmetE mutants. The ZEA concentration is indicated next to each panel. Photographs were taken 3 days after inoculation.
Figure 7:
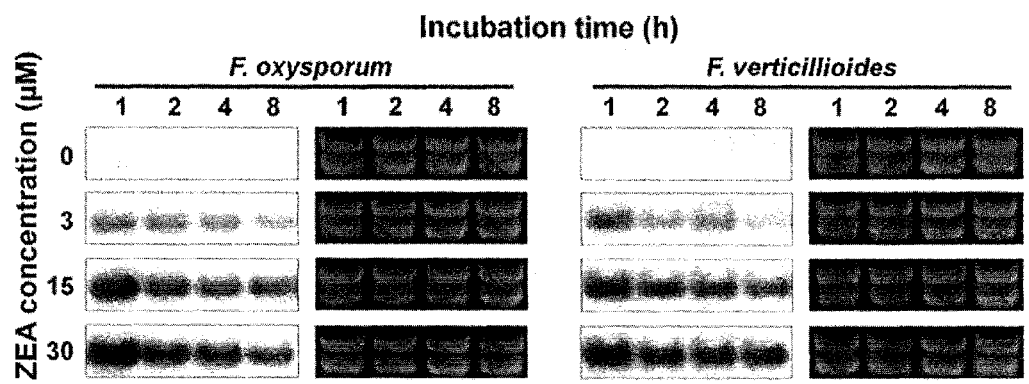
FIG. 7 is a photograph showing expression profiles of ZEAR homolog in *F. oxysporum* and *F. verticillioides*. Total RNA of each strain was extracted from CM cultures grown for 1, 2, 4, and 8 h after ZEA treatment. Twenty micrograms of total RNA was subjected to Northern analysis, with the PCR product of FOXG_13654.2 and FVEG_11090.3, amplified from *F. oxysporum* strain F00901 and *F. verticillioides* strain FV0201, respectively, with Fzear-orf1/Fzear-orf2 primers, serving as a probe. An ethidium-bromide-stained gel is shown as a loading control.
Figure 8:
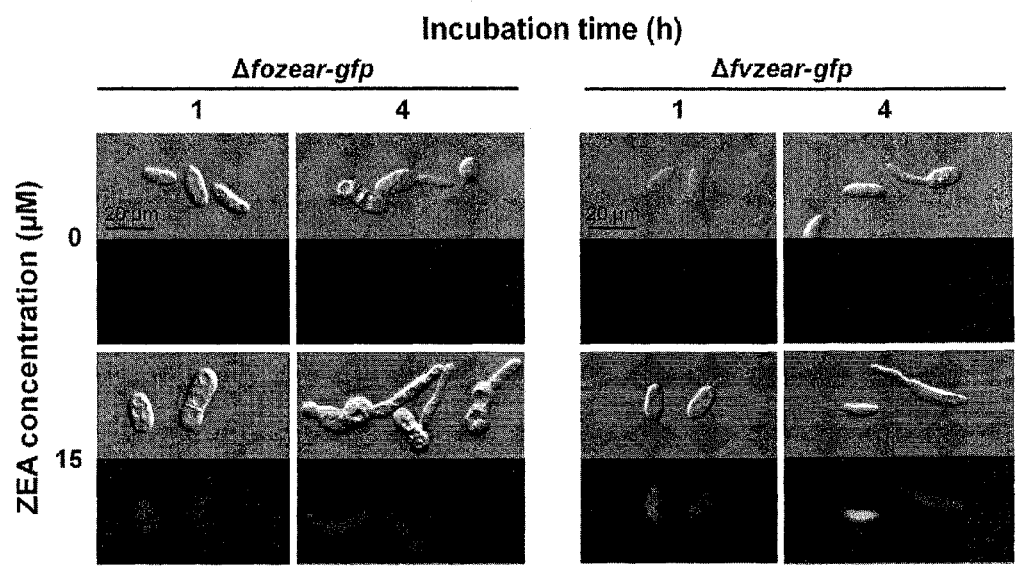
FIG. 8 is a photograph showing the results of GFP expression of Δfozear-gfp and Δfvzear-gfp mutants. FOXG_13654.2 and FVEG_11090.3 from *F. oxysporum* and *F. verticillioides*, respectively, were replaced with GFP and hph to generate the Δfozear-gfp and Δfvzear-gfp mutants. Conidia were incubated for 1 and 4 h in CM supplemented with ZEA. First and third lines, bright-field microscopy; Second and fourth lines, fluorescence microscopy.

In one aspect of this invention, there is provided a zearalenone-inducible promoter.

The present invention is related to a specific promoter that is isolated from *Gibberella zeae*, and more specifically, the promoter comprises a nucleotide sequence of SEQ ID NO: 1. The promoter originated from 847 bp of 5' and 3' flanking regions of FGSG-04581.3 gene, ZEAR (zearalenone response gene) designated by the present inventors.

Further, variants of the said promoter sequence are within the scope of the present invention. The variants have a different nucleotide sequence but have similar functional characteristics to those of the nucleotide sequence of SEQ ID NO: 1. Specifically, the promoter of the present invention may comprise a nucleotide sequence within at least 70%, preferably at least 80%, more preferably at least 90%, and most preferably at least 95% homology with the nucleotide sequence of SEQ ID NO: 1.

The "sequence homology %" for certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

In the second aspect of this invention, there is provided a recombinant vector comprising the zearalenone-inducible promoter.

The term "vector" is used herein to refer DNA fragment (s) and nucleotide molecules that are delivered to a cell. Vector can be used for the replication of DNA and be independently reproduced in a host cell. The term "expression vector" and "vector" are often interchangeably used. The term "expression vector" means a recombinant DNA molecule comprising a desired coding sequence and other appropriate nucleotide sequences that are essential for the expression of the operatively-linked coding sequence in a specific host organism. Promoter, enhancer, termination codon and polyadenylation signal that can be used for a eukaryotic cell are well known in the pertinent art. The vector system of this invention may be performed by various methods known to those skilled in the art and its practical method is described in Sambrook et al., *Molecular Cloning, A Laboratory Manual*, Cold Spring Harbor Laboratory Press (2001), which is herein incorporated by reference.

According to a preferred embodiment, the recombinant vector further comprises a gene encoding a target protein which is operatively linked to the promoter.

The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The target protein can be any kind of protein, preferably a protein encoded by a foreign gene, and examples thereof include a peptide, a polypeptide, a structural protein, a regulatory protein, a binding protein, a signal protein, an adhesion protein, a toxin, an enzyme, a hormone, an antibody, an antigen, a cytokine, etc., but not limited to.

According to a preferred embodiment, the target protein is a reporter protein, more preferably a fluorescent protein, still more preferably a green fluorescent protein (GFP), a yellow fluorescent protein (YFP), a red fluorescent protein (RFP), a GFP-derived variant protein, a luciferase or a β-glucuronidase, most preferably a GFP.

The term "foreign gene" means a gene to be not present in nature plants or microorganisms. The foreign gene may be a modified form of a gene or genes present in other nature plants or microorganisms, an artificially-synthesized form or a fused form of two or more genes. The plants or microorganisms containing these foreign genes may express gene products not to be produced in nature.

To prepare artificially-synthesized genes, DNA synthesis technique and nucleic acid chemical method are used. For instance, the methods described in Gait, M. J. (1985) Oligonucleotide Synthesis: A Practical Approach, IRL Press; Gait, M. J. (1990) Oligonucleotide Synthesis: A Practical Approach, IRL Press; Eckstein, F. (1991) Oligonucleotides and Analogues: A Practical Approach, IRL Press; Adams, R. L. et al., (1992) The Biochemistry of the Nucleic Acids, Chapman & Hall; Shabarova, Z. et al., (1994) Advanced Organic Chemistry of Nucleic Acids, Weinheim; Blackburn, G. M. et al., (1996) Nucleic Acids in Chemistry and Biology, Oxford University Press; and Hermanson, G. T. (1996) Bioconjugate Techniques, Academic Press are utilized, the disclosure of which is herein incorporated by references.

The foreign gene of this invention includes any gene encoding a suitable protein to be massively expressed in plants or microorganisms, for example, peptides with pharmacological efficacies, hormones, vaccine antibodies, peptides useful in agriculture such as anti-bacteria protein, various enzymes synthesizing secondary metabolites, inhibitors regulating enzyme activity or enzymes required for process of bioethanol production (e.g., cellulase, hemicellulase or pectinase), but not limited to.

In addition, the present vector includes antibiotics (example: neomycin, carbenicillin, kanamycin, spectinomycin, hygromycin, etc.)-resistant genes (example: neomycin phosphotransferase (nptII), hygromycin phosphotransferase (hpt), etc.) as a selection marker.

In the third aspect of this invention, there is provided a transformant transformed with the recombinant vector comprising the zearalenone-inducible promoter.

According to a preferred embodiment, the transformant is a recombinant microorganism or plant. Methods of transforming the microorganism or plant are well known in the art. Preferably, the recombinant microorganism is *Gibberella zeae*, but not limited to. Preferably, the recombinant plant is a transformed plant that can recognize a *Gibberella zeae* attack, but not limited to.

In the forth aspect of this invention, there is provided a method of producing a protein comprising the steps of (a) culturing the recombinant microorganism in a medium containing zearalenone and expressing a target gene in the medium; and (b) isolating the protein prepared by the target gene expression.

The culture of recombinant microorganisms could be carried out by various methods known to those skilled in the art. The detailed description to culture of microorganisms is disclosed in Kubitschek, H. E., Introduction to Research with Continuous Cultures. Englewood Cliffs, N.J.: Prentice-Hall, Inc., 1970; Mandelstam, J., et al., Biochemistry of Bacterial Growth, 3rd ed. Oxford:Blackwell, 1982; Meynell, G. G., et al., Theory and Practice in Experimental Bacteriology, 2nd ed. Cambridge: Cambridge University Press, 1970; and Gerhardts, P., ed., Manual of Methods for General Bacteriology, Washington: *Am. Soc. Microbiol,* 1981, which are herein incorporated by reference.

The methods of isolating the protein includes chemical methods, methods of collecting recombinant proteins in cell lysate, etc., but not limited to.

In the fifth aspect of this invention, there is provided a method of detecting a plant contaminated with zearalenone, which comprises the steps of (a) crushing the plant; (b) mixing the crushed plant into a medium; (c) culturing the microorganism in the medium; and (d) detecting a reporter protein of ZEA in the microorganism or medium.

According to a preferred embodiment, the microorganism is a recombinant microorganism transformed with a recombinant vector comprising a gene encoding a fluorescent protein and the reporter protein is fluorescent.

In the sixth aspect of this invention, there is provided a system for detecting a plant contaminated with zearalenone, which comprises the zearalenone-inducible promoter.

The system of this invention includes any system can detect the plant contaminated with zearalenone. Preferably, the system is a kit or biosensors.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

Fungal Strains and Media

The *G. zeae* strain GZ03639 was provided by Robert L. Bowden (U.S. Department of Agriculture-Agricultural Research Service, Manhattan, Kans.). The *Fusarium oxysporum* strain F00901 and *F. verticillioides* strain FV0201 were isolated from South Korea and used as wild-type strains. The *G. zeae* methionine ΔGzmetE auxotroph strain, which was previously generated (6), was used as a negative control for the promoter replacement experiments. All strains used in this study were stored as frozen conidial suspensions in 15% glycerol at −70° C. For DNA and RNA extractions, strains were grown in 25 ml of complete medium (CM) or minimal medium (MM) (17). Conidia were produced on yeast malt agar (YMA) (7). The growth rates of strains were tested on CM, MM, and potato dextrose agar (PDA) (17), and strains were grown on rice medium for toxin production (15). To test for activity of an inducible promoter, strains were inoculated on CM and MM supplemented with 0, 3, 15, and 30 μM ZEA or 0.25 mM methionine (Sigma-Aldrich, St. Louis, Mo.).

Nucleic Acid Manipulations, Primers, and PCR Conditions

Fungal genomic DNA and total RNA were prepared using a cetyl trimethyl ammonium bromide protocol (17) and the Trizol reagent (Invitrogen, Carlsbad, Calif.), respectively. Standard procedures were used for restriction endonuclease digestion, agarose gel electrophoresis, and Southern and Northern blot hybridization (28). One hundred ng of PCR product was labeled with [α-$^{32}$P]dCTP by random priming and was used as a probe in the Southern and Northern blot analyses. Hybridization was carried out at 65° C. for 18 h. The general PCR was performed as previously described (14). The PCR primers (Table 1) used in the present invention were synthesized by the Bioneer oligonucleotide synthesis facility (Bioneer, Daejon, South Korea).

TABLE 1

Primers used in the present invention

| Primer | Sequence (5'-3') | |
|---|---|---|
| gfp-f1-zear | GAGAGAACGAAAGTAACCATGGTGAGCAAGGGCGAGGAGC | (SEQ ID NO: 2) |
| hph-f1 | GGCTTGGCTGGAGCTAGTGGAGG | (SEQ ID NO: 3) |
| hph-r2 | AACCCGCGGTCGGCATCTACTCTA | (SEQ ID NO: 4) |
| hph-f3 | GATGTAGGAGGGCGTGGATATGT | (SEQ ID NO: 5) |
| hph-r4 | GAACCCGCTCGTCTGGCTAAG | (SEQ ID NO: 6) |
| zear-f1 | GAGCGTGTCACCTACCGAGAGC | (SEQ ID NO: 7) |
| zear-f1-nt | CATGCCCTGGCGTTGAAGTT | (SEQ ID NO: 8) |
| zear-r2-gfp | CCTCGCCCTTGCTCACCATGGTTACTTTCGTTCTCTCTGG | (SEQ ID NO: 9) |

TABLE 1-continued Primers used in the present invention

| Primer | Sequence (5'-3') | |
|---|---|---|
| zear-f3-hph | CCTCCACTAGCTCCAGCCAAGCCTAATTTGGCGTTGGTTGGTCTT | (SEQ ID NO: 10) |
| zear-r4 | ACGATCCCGGTGCTTGGTT | (SEQ ID NO: 11) |
| zear-r4-nt | TGGTTCCGTGCCGTTTGTGATA | (SEQ ID NO: 12) |
| zear-orf1 | ATGGCTTCTGATCAGCAACGCC | (SEQ ID NO: 13) |
| zear-orf2 | TCATGCCTCCATCTTCTCTCTTTC | (SEQ ID NO: 14) |
| Pzear-f1-hph | TAGAGTAGATGCCGACCGCGGGTTCATGCCCTGGCGTTGAAGTT | (SEQ ID NO: 15) |
| Pzear-r2 | GGTTACTTTCGTTCTCTCTGGTCT | (SEQ ID NO: 16) |
| gzmetE-f1 | GCGGTGGTACGTAAGTCGGTTTCT | (SEQ ID NO: 17) |
| gzmetE-f1-nt | CGTGCTGCCCGAGTGAAGTTT | (SEQ ID NO: 18) |
| gzmetE-r2-hph | TCCACTAGCTCCAGCCAAGCCGGTATGGCGTAATTCTGCTTGG | (SEQ ID NO: 19) |
| gzmetE-f3-Pzear | GAGAGAACGAAAGTAACCATGTCAGAAATCAACACTACAAACGG | (SEQ ID NO: 20) |
| gzmetE-r4 | ATGGCCGTCGTTGTGGATTTG | (SEQ ID NO: 21) |
| gzmetE-r4-nt | ACTTGGGGTCGGCGTAGATGC | (SEQ ID NO: 22) |
| gzmetE-orf1 | TGTTGTCAAGCGCACCTCCATA | (SEQ ID NO: 23) |
| gzmetE-orf2 | CTGCGCGATCTCCTCTTGTTC | (SEQ ID NO: 24) |
| Fzear-orf1 | ATGGCACCCGAACAACAACGAC | (SEQ ID NO: 25) |
| Fzear-orf2 | CCTGATGCCTCTCATCAGGACTC | (SEQ ID NO: 26) |
| Fozear-f1 | TCGTCGTGGGCTTCATGTTGTAGA | (SEQ ID NO: 27) |
| Fozear-f1-nt | TGGTCGATGTTGGGCGGTAAGT | (SEQ ID NO: 28) |
| Fozear-r2-gfp | CGCCCTTGCTCACCATGGTTTGTGTTATACGATAAGCCACTAGCCG | (SEQ ID NO: 29) |
| Fozear-f3-hph | CCTCCACTAGCTCCAGCCAAGCCATGCGCTTGCTACGGGGACAG | (SEQ ID NO: 30) |
| Fozear-r4 | ACCAAAAGACGATGAGGGTGCTATC | (SEQ ID NO: 31) |
| Fozear-r4-nt | AGCCTCTCCTGAAATTGCTAAACGA | (SEQ ID NO: 32) |
| Fvzear-f1 | CCTCAGCGGTGTAGATAGTTTCTCCC | (SEQ ID NO: 33) |
| Fvzear-f1-nt | GTTTCTCCCCTGTGATGCTTGTGC | (SEQ ID NO: 34) |
| Fvzear-r2-gfp | CGCCCTTGCTCACCATGGTTTATGCTTATACGATATGCGCACTAGC | (SEQ ID NO: 35) |
| Fvzear-f3-hph | CCTCCACTAGCTCCAGCCAAGCCGGGTATTGGGTTATTGGGGAGTTCAT | (SEQ ID NO: 36) |
| Fvzear-r4 | TCCCCAGAATTTCCCCAACAATG | (SEQ ID NO: 37) |
| Fvzear-r4-nt | TAGGTCCAGGCCGCCATACTG | (SEQ ID NO: 38) |

Targeted Gene Deletion Using GFP Reporter Constructs

A green fluorescent protein (GFP) reporter construct was created by double-joint PCR (38). A gfp-hph fragment (2.7 kb) that carries a GFP open reading frame (ORF) and hygromycin phosphotransferase cassette (hph) was amplified from pIGPAPA (8) with gfp-f1-zear/hph-f1 primers (Table 1). The 5' and 3' flanking regions of ZEAR (Broad Institute; FGSG_04581.3) were amplified by PCR from the wildtype strain GZ03639 with the zear-f1/zear-r2-gfp and zear-f3-hph/zear-r4 primers, respectively. The PCR amplification conditions were 2 min at 94° C., followed by 30 cycles of 30 s at 94° C., 1 min at 55° C., and 2 min at 72° C., followed by a final extension for 10 min at 72° C. The PCR products were purified with the DNA purification system (Promega, Madison, Wis.) using the manufacturer's instructions. The three amplicons were fused by PCR in a 25 µl reaction mixture containing 2 µl of the 5'-flanking amplicon (50 ng/µl), 2 µl of the 3'-flanking amplicon (50 ng/µl), 3 µl of the hph amplicon (100 ng/µl), 2 µl of deoxynucleoside triphosphates (dNTPs) (2.5 mM each), 2.5 µl of 10×PCR buffer including MgCl$_2$, 1 U of ExTaq polymerase (Takara Bio Inc., Japan), and 13.25 µl of water. The PCR amplification conditions were 2 min at 94° C., followed by 10 cycles of 30 s at 94° C., 20 min at 58° C., and 5 min at 72° C., followed by a final extension of 10 min at 72° C. One µl of this amplification mixture was reamplified as a template in PCRs with zear-f1-nt/hph-f3 and hph-r4/zear-r4-nt primer sets and a 50-μl reaction volume. The PCR conditions were 2 min at 94° C., followed by 30 cycles of 30 s at 94° C., 1 min at 60° C., and 3 min at 72° C., followed by a final extension for 10 min at 72° C. Constructs for *F. oxysporum* and *F. verticillioides* were created using the same approach. These amplification products were combined and used to directly transform fungal protoplasts using a polyethylene glycol (PEG)-mediated method (15).

Promoter Replacement with an Inducible Promoter

The 5' flanking region of the GzmetE (Broad Institute; FGSG_05658.3) gene, which is essential for methionine biosynthesis in *G. zeae* and deletion of which causes methionine auxotrophy (6), was replaced with the 5' flanking region of ZEAR. The hph (1.4 kb) gene was amplified from pIGPAPA with the hph-f1/hph-r2 primer pairs. An 838-bp fragment corresponding to the −838 to −1 bp region of the ZEAR translational start site was amplified from the wild-type strain GZ03639 with the Pzear-f1-hph/Pzear-r2 primers. The 5' flanking region and ORF of GzmetE were amplified from the wild-type strain with the gzmetE-f1/gzmetE-r2-hph and gzmetE-f3-Pzear/gzmetE-r4 primer sets, respectively. After PCR purification, the four PCR products were fused by PCR, and 1 μl of this amplification mixture was reamplified as a template in PCRs with the gzmetE-f1-nt/hph-r3 and hphr4/gzmetE-r4-nt primer sets. These amplification products were transformed into protoplasts of the wild-type strain GZ03639.

Expression Profiles of Genes in Response to ZEA Treatment

Strains were incubated in 25 ml CM for 72 h at 24° C. on a rotary shaker (150 rpm), and mycelia harvested through filtration subsequently were washed twice with 50 ml of sterile, distilled water. The mycelia were reincubated in 25 ml CM or MM supplemented with 0, 3, 15, and 30 μM ZEA, and total RNA was extracted from the cultures at 1, 2, 4, and 8 h after ZEA treatment for Northern blot analysis. PCR fragments amplified from the wild-type strains with the zear-orf1/zear-orf2, gzmetE-orf1/gzmetE-orf2, and Fzear-orf1/Fzear-orf2 primer sets were used as probes for analyzing transcript levels of ZEAR, GzmetE, and ZEAR homologs, respectively.

Microscopic Observation

Conidia ($10^5$) produced on YMA were reincubated in 3 ml of CM supplemented with 0, 3, 6, 9, 12, 15, 30, 300, 1,500, and 3,000 μM ZEA and observed at 1, 2, 4, and 8 h after inoculation with a DE/Axio Imager A1 microscope (Carl Zeiss, Oberkochen, Germany) with excitation and emission wavelengths of 488 and 515/530 nm, respectively.

Results

Identification of ZEA-Inducible Genes

The present inventors previously performed a microarray analysis to characterize the biological functions of ZEA in *G. zeae*. To synthesize cDNA for the microarray analysis, the wild-type strain GZ03639 of *G. zeae* was grown in 25 ml of an SG medium (1), which is used for ZEA production by *G. zeae*, and supplemented with 0 or 15 μM ZEA for 3 days at 24° C. (Lee et al., unpublished). Interestingly, the expression level of ZEAR (Broad Institute; FGSG_04581.3) in the SG culture supplemented with 15 μM ZEA was 50 times higher than that in the SG culture without ZEA. The present inventors hypothesized that this gene was induced by ZEA treatment and that the promoter of the gene could be developed as an inducible promoter in *G. zeae*. Since *G. zeae* does not produce ZEA when grown in CM, we confirmed our hypothesis by performing Northern blot analysis of RNA extracted from the CM culture treated with exogenous ZEA. The expression of ZEAR markedly increased in the CM culture after 1 h of ZEA treatment and subsequently decreased over time. The transcript was not detected in the culture without ZEA treatment. In addition, the level of ZEAR expression was dependent on the ZEA concentration used (FIG. 1). This result supported the hypothesis that expression of ZEAR was induced by ZEA. Moreover, the expression profile of the gene satisfied the requirements for an inducible promoter since the gene expression rapidly increased upon ZEA treatment and was not detected in the control. We designated the promoter of ZEAR Pzear.

ZEAR is a putative 114-amino-acid fungus-specific C6 transcription factor that contains one intron and an N-terminal fungal transcriptional regulatory domain (amino acid residues 1 to 54). It also contains a nuclear localization signal (KRSRRKP; amino acid residues 48 to 54) located at the end of the transcriptional regulatory domain. ZEAR is not conserved in plants and animals but is highly conserved in the genus *Fusarium*. However, the functions of the gene have not been characterized for any of the fungal species.

In addition to ZEAR, the present inventors also selected another putative transcription factor, called ZEB2 (Broad Institute; FGSG_02398.3), which controlled the ZEA gene cluster (12). Expression of ZEB2 was five times higher in SG cultures supplemented with 15 μM ZEA than in the SG culture without ZEA. Our previous study showed that ZEB2 expression gradually increased over time in wild-type *G. zeae* cultured in SG medium but was low in the ZEA-nonproducing mutants (12). However, in contrast to that of ZEAR, the expression of ZEB2 was not rapidly induced by ZEA treatment, suggesting that the ZEB2 promoter would not be suitable for a conditional system that used a ZEA-responsive inducible promoter.

Targeted Gene Deletion Using GFP Reporter Constructs

The ZEAR ORF was replaced with GFP and hph by targeted deletion. Positive mutant clones were confirmed by the presence of a 6.3-kb band on a Southern blot (FIG. 2). The wild-type construct migrated as a 4.0-kb band. The Δzear-gfp deletion mutant did not show any noticeable phenotypic changes in the following characteristics: growth rate, mycelial morphology on MM, CM, and PDA, conidiation and conidial morphology on YMA, sexual reproduction on carrot agar, trichothecene and ZEA production on rice culture, and pathogenicity in wheat. Further, the mutant had no phenotypic changes under the following stress conditions: NaCl, KCl, sorbitol, $FeSO_4$, menadione, fludioxonil, iprodione, sodium dodecyl sulfate (SDS), Congo red, benomyl, and acidic (pH 4) and basic (pH 11) conditions).

Microscopic observation showed that GFP in the Δzear-gfp mutant was not expressed in the control CM culture without ZEA but was detected at the 1-h time point in cultures treated with ZEA (FIG. 3). The level of GFP expression was dependent on the ZEA concentration used: it was gradually elevated in response to 3 to 30 μM ZEA but decreased at ZEA concentrations higher than 30 μM. Further, expression of GFP in these cultures decreased over time.

Promoter Replacement

The promoter of the GzmetE gene was replaced with Pzear, which corresponded to a −838 to −1 bp region of the ZEAR translational start site, and confirmed by Southern blotting. Positive mutants (Pzear-GzmetE) that contained Pzear fused to GzmetE showed a 3.3-kb band, in contrast to the wild type, which showed a 1.5-kb band (FIG. 4). The GzmetE gene was constitutively transcribed in the wildtype strain regardless of the ZEA concentration, while the expression of GzmetE from the Pzear-GzmetE mutant exhibited a rapid increase after ZEA treatment followed by a decrease over time (FIG. 5). Expression of GzmetE was dependent on the concentration of ZEA in a manner similar to that of ZEAR expression.

To confirm that the Pzear promoter fused to GzmetE regulated the expression of GzmetE in Pzear-GzmetE mutants, we inoculated those strains on MM supplemented with ZEA. The Pzear-GzmetE and ΔgzmetE mutants did not grow on MM without ZEA compared to the wild-type control. The mutants did grow on MM supplemented with 3 μM ZEA; however, radial growth was not completely recovered. In contrast, radial growth of the mutants did recover to a level comparable to that of the wild-type strain when grown on MM supplemented with 15 and 30 μM ZEA (FIG. 6). These data suggested that GzmetE expression in the mutants was fully induced by ZEA treatment.

Identification of ZEAR Homologs in *F. oxysporum* and *F. verticillioides*

Homologs of ZEAR were identified from the Fusarium Comparative Database of the Broad Institute at Caambrgide, Mass by a BlastP search.Protein sequences of FOXG_13654.2 and FVEG 11090.3 from *F. oxysporum* and *F. verticillioides*, respectively, which share 96% identity, had 74% identity with ZEAR. Expression of FOXG_13654.2 and FVEG_11090.3 increased in the CM culture after 1 h of ZEA treatment and decreased over time, similar to ZEAR expression in *G. zeae*. The transcripts were not detected in the culture without ZEA treatment but increased in a ZEA dose-dependent manner (FIG. 7). FOXG_13654.2 and FVEG_11090.3 were then replaced with GFP and hph, and positive mutant clones were confirmed by Southern blotting. FOXG_13654.2 and FVEG_11090.3 deletion mutants designated the Δfozear-gfp and Δfvzear-gfp mutants, respectively, did not show any noticeable phenotypic changes. Microscopic observation showed that GFP in the Δfozear-gfp and Δfvzear-gfp mutants was not expressed in the control CM culture without ZEA but was detected at the 1-h time point in cultures treated with ZEA (FIG. 8), showing that the level of GFP expression in the mutants was similar to that in the Δzear-gfp mutant. This result suggested that expression of FOXG_13654.2 and FVEG_11090.3 is induced by ZEA and that the promoters of these genes are useful in a conditional expression system in *F. oxysporum* and *F. Verticillioides.*

Industrial Applicability

In the present invention, the promoter replacement method using the Pzear promoter successfully restored the growth of an auxotroph mutant when ZEA was supplied to MM lacking methionine, suggesting that this promoter may be useful in a conditional gene expression system exogenously treated with ZEA. In addition, our data suggest that this method can be used for studying essential genes in this fungus. For example, addition of ZEA during fungal transformation would allow mutants that carry the Pzear promoter fused to an essential target gene to survive.

The cellular function of the target gene could also be characterized by adjusting the amount of ZEA supplemented in the phenotyping media.

The conditional system described in the present invention could also be used for characterizing the mechanism of self/nonself recognition in *G. zeae.*

The approach developed in this study may also be applicable for the genetic engineering of plant systems to generate plants that can recognize a *G. zeae* attack.

Another possible application for this system is as a biosensor for the detection of ZEA contamination.

References

1. Bacon, C. W., J. D. Robbins, and J. K. Porter. 1977. Media for identification of *Gibberella zeae* and production of F-2-(Zearalenone). Appl. Environ. Microbiol. 33:445-449.
2. Chevanne, D., E. Bastiaans, A. Debets, S. J. Saupe, C. Clave, and M. Paoletti. 2009. Identification of the het-r vegetative incompatibility gene of *Podospora anserina* as a member of the fast evolving HNWD gene family. Curr. Genet. 55:93-102.
3. Desjardins, A. E. 2006. *Fusarium* mycotoxins: chemistry, genetics and biology. APS Press, St. Paul, Minn.
4. Gaffoor, I., and F. Trail. 2006. Characterization of two polyketide synthase genes involved in zearalenone biosynthesis in *Gibberella zeae*. Appl. Environ. Microbiol. 72:1793-1799.
5. Gebhart, D., A. K. Bahrami, and A. Sil. 2006. Identification of a copperinducible promoter for use in ectopic expression in the fungal pathogen *Histoplasma capsulatum*. Eukaryot. Cell 5:935-944.
6. Han, Y.-K., T. Lee, K.-H. Han, S.-H. Yun, and Y.-W. Lee. 2004. Functional analysis of the homoserine O-acetyltransferase gene and its identification as a selectable marker in *Gibberella zeae*. Curr. Genet. 46:205-212.
7. Harris, S. D. 2005. Morphogenesis in germinating *Fusarium graminearum* macroconidia. Mycologia 97:880-887.
8. Horwitz, B. A., A. Sharon, S. W. Lu, V. Ritter, T. M. Sandrock, O. C. Yoder, and B. G. Turgeon. 1999. A G protein alpha subunit from *Cochliobolus heterostrophus* involved in mating and appressorium formation. Fungal Genet. Biol. 26:19-32.
9. Hou, Z., C. Xue, Y. Peng, T. Katan, H. C. Kistler, and J.-R. Xu. 2002. A mitogen-activated protein kinase gene (MGV1) in *Fusarium graminearum* is required for female fertility, heterokaryon formation, and plant infection. Mol. Plant Microbe Interact. 15:1119-1127.
10. Jurgenson, J. E., R. L. Bowden, K. A. Zeller, J. F. Leslie, N. J. Alexander, and R. D. Plattner. 2002. A genetic map of *Gibberella zeae* (*Fusarium graminearum*). Genetics 160: 1451-1460.
11. Kim, J.-E., J. Jin, H. Kim, J.-C. Kim, S.-H. Yun, and Y.-W. Lee. 2006. GIP2, a putative transcription factor that regulates the aurofusarin biosynthetic gene cluster in *Gibberella zeae*. Appl. Environ. Microbiol. 72:1645-1652.
12. Kim, Y.-T., Y.-R. Lee, J. Jin, K.-H. Han, H. Kim, J.-C. Kim, T. Lee, S.-H. Yun, and Y.-W. Lee. 2005. Two different polyketide synthase genes are required for synthesis of zearalenone in *Gibberella zeae*. Mol. Microbiol. 58:1102-1113.
13. Lee, J., J. E. Jurgenson, J. F. Leslie, and R. L. Bowden. 2008. Alignment of genetic and physical maps of *Gibberella zeae*. Appl. Environ. Microbiol. 74:2349-2359.
14. Lee, J., J. F. Leslie, and R. L. Bowden. 2008. Expression and function of sex pheromones and receptors in the homothallic ascomycete *Gibberella zeae*. Eukaryot. Cell 7:1211-1221.
15. Lee, T., Y.-K. Han, K.-H. Kim, S.-H. Yun, and Y.-W. Lee. 2002. Tri13 and Tri7 determine deoxynivalenol- and nivalenol-producing chemotypes of *Gibberella zeae*. Appl. Environ. Microbiol. 68:2148-2154.
16. Leslie, J. F. 1993. Fungal vegetative compatibility. Annu. Rev. Phytopathol. 31:127-150.
17. Leslie, J. F., and B. A. Summerell. 2006. The *Fusarium* laboratory manual. Blackwell Professional, Ames, Iowa.
18. Lysøe, E., K. R. Bone, and S. S. Klemsdal. 2009. Real-time quantitative expression studies of the zearalenone biosynthetic gene cluster in *Fusarium graminearum*. Phytopathology 99:176-184.
19. Lysøe, E., S. S. Klemsdal, K. R. Bone, R. J. Frandsen, T. Johansen, U. Thrane, and H. Giese. 2006. The PKS4 gene of *Fusarium graminearum* is essential for zearalenone production. Appl. Environ. Microbiol. 72:3924-3932.

20. Mach, R. L., and S. Zeilinger. 2003. Regulation of gene expression in industrial fungi: *Trichoderma*. Appl. Microbiol. Biotechnol. 60:515-522.
21. Micali, C. O., and M. L. Smith. 2006. A nonself recognition gene complex in *Neurospora crassa*. Genetics 173: 1991-2004.
22. Mirocha, C. J., and C. M. Christensen. 1974. Oestrogenic mycotoxins synthesized by *Fusarium* sp., p. 129-148. In I. F. H. Purchase (ed.), Mycotoxins. Elsevier Scientific Publishing, Amsterdam, Netherlands.
23. Munson, G. P., D. L. Lam, F. W. Outten, and T. V. O'Halloran. 2000. Identification of a copper-responsive two-component system on the chromosome of *Escherichia coli* K-12. J. Bacteriol. 182:5869-5871.
24. Osusky, M., G. Zhou, L. Osuska, R. E. Hancock, W. W. Kay, and S. Misra. 2000. Transgenic plants expressing cationic peptide chimeras exhibit broadspectrum resistance to phytopathogens. Nat. Biotechnol. 18:1162-1166.
25. Park, J. N., M. J. Sohn, D. B. Oh, O. Kwon, S. K. Rhee, C. G. Hur, S. Y. Lee, G. Gellissen, and H. A. Kang. 2007. Identification of the cadmium-inducible *Hansenula polymorpha* SEO1 gene promoter by transcriptome analysis and its application to whole-cell heavy-metal detection systems. Appl. Environ. Microbiol. 73:5990-6000.
26. Proctor, R. H., T. M. Hohn, and S. P. McCormick. 1995. Reduced virulence of *Gibberella zeae* caused by disruption of a trichothecene toxin biosynthetic gene. Mol. Plant Microbe Interact. 8:593-601.
27. Romero, B., G. Turner, I. Olivas, F. Laborda, and J. R. De Lucas. 2003. The *Aspergillus nidulans* alcA promoter drives tightly regulated conditional gene expression in *Aspergillus fumigatus* permitting validation of essential genes in this human pathogen. Fungal Genet. Biol. 40:103-114.
28. Sambrook, J. S., and D. Russell. 2001. Molecular cloning: a laboratory manual, 3rd ed. Cold Spring Harbor Laboratory Press, Cold Spring Harbor, N.Y.
29. Seong, K., Z. Hou, M. Tracy, H. C. Kistler, and J.-R. Xu. 2005. Random insertional mutagenesis identifies genes associated with virulence in the wheat scab fungus *Fusarium graminearum*. Phytopathology 95:744-750.
30. Shoji, J.-Y., J.-I. Maruyama, M. Arioka, and K. Kitamoto. 2005. Development of *Aspergillus oryzae* thiA promoter as a tool for molecular biological studies. FEMS Microbiol. Lett. 244:41-46.
31. Skadsen, R. W., P. Sathish, M. L. Federico, T. Abebe, J. Fu, and H. F. Kaeppler. 2002. Cloning of the promoter for a novel barley gene, Lem1, and its organ-specific promotion of GFP expression in lemma and palea. Plant Mol. Biol. 49:545-555.
32. Tada, S., K. Gomi, K. Kitamoto, K. Takahashi, G. Tamura, and S. Hara. 1991. Construction of a fusion gene comprising the Taka-amylase A promoter and the *Escherichia coli* beta-glucuronidase gene and analysis of its expression in *Aspergillus oryzae*. Mol. Gen. Genet. 229:301-306.
33. Verma, N., and M. Singh. 2005. Biosensors for heavy metals. Biometals 18:121-129.
34. Waring, R. B., G. S. May, and N. R. Morris. 1989. Characterization of an inducible expression system in *Aspergillus nidulans* using a/cA and tubulincoding genes. Gene 79:119-130.
35. Willyerd, K. L., A. M. Kemp, and A. L. Dawe. 2009. Controlled gene expression in the plant pathogen *Cryphonectria parasitica* by use of a copperresponsive element. Appl. Environ. Microbiol. 75:5417-5420.
36. Yevtushenko, D. P., V. A. Sidorov, R. Romero, W. W. Kay, and S. Misra. 2004. Wound-inducible promoter from poplar is responsive to fungal infection in transgenic potato. Plant Sci. 167:715-724.
37. Yu, H.-Y., J.-A. Seo, J.-E. Kim, K.-H. Han, W.-B. Shim, S.-H. Yun, and Y.-W. Lee. 2008. Functional analyses of heterotrimeric G protein G alpha and G beta subunits in *Gibberella zeae*. Microbiology 154:392-401.
38. Yu, J.-H., Z. Hamari, K.-H. Han, J.-A. Seo, Y. Reyes-Dominguez, and C. Scazzocchio. 2004. Double-joint PCR: a PCR-based molecular tool for gene manipulations in filamentous fungi. Fungal Genet. Biol. 41:973-981.
39. Zuo, J., P. D. Hare, and N. H. Chua. 2006. Applications of chemical-inducible expression systems in functional genomics and biotechnology. Methods Mol. Biol. 323: 329-342.

What is claimed is:

1. A zearalenone-inducible promoter comprising the nucleotide sequence of SEQ ID NO:1 wherein said promoter is linked to heterologous DNA.

2. A recombinant vector, which comprises the promoter of claim 1.

3. The recombinant vector according to claim 2, wherein the vector further comprises a gene encoding a target protein which is operatively linked to the promoter.

4. The recombinant vector according to claim 3, wherein the target protein is a reporter protein.

5. The recombinant vector according to claim 4, wherein the reporter protein is a fluorescent protein.

6. A recombinant microorganism, which is transformed with the recombinant vector according to claim 2.

7. A plant, which is transformed with the recombinant vector according to claim 2.

8. A method of producing a protein, which comprises the steps of (a) culturing the recombinant microorganism of claim 6 in a medium containing zearalenone and expressing a target gene operably linked to the promoter in the medium; and (b) isolating the protein prepared by the target gene expression.

9. A method of detecting a plant contaminated with zearalenone, which comprises the steps of (a) crushing the plant; (b) mixing the crushed plant into a medium; (c) culturing the microorganism of claim 6 in the medium; and (d) detecting a reporter protein of zearalenone in the microorganism or medium.

10. The method according to claim 9, wherein the microorganism of claim 6 is a recombinant microorganism transformed with a recombinant vector comprising a gene encoding a fluorescent protein and the reporter protein is fluorescent.

11. A kit for detecting a plant contaminated with zearalenone, which comprises the promoter of claim 1.

12. A recombinant microorganism, which is transformed with the recombinant vector according to claim 3.

13. A recombinant microorganism, which is transformed with the recombinant vector according to claim 4.

14. A recombinant microorganism, which is transformed with the recombinant vector according to claim 5.

15. A plant, which is transformed with the recombinant vector according to claim 3.

16. A plant, which is transformed with the recombinant vector according to claim 4.

17. A plant, which is transformed with the recombinant vector according to claim 5.

18. A method of producing a protein, which comprises the steps of (a) culturing the recombinant microorganism of claim 12 in a medium containing zearalenone and expressing the target gene in the medium; and (b) isolating the protein prepared by the target gene expression.

19. A method of producing a protein, which comprises the steps of (a) culturing the recombinant microorganism of claim 13 in a medium containing zearalenone and expressing the target gene in the medium; and (b) isolating the protein prepared by the target gene expression.

20. A method of producing a protein, which comprises the steps of (a) culturing the recombinant microorganism of claim 14 in a medium containing zearalenone and expressing the target gene in the medium; and (b) isolating the protein prepared by the target gene expression.

* * * * *

SEQUENCE LISTING

```
<160> NUMBER OF SEQ ID NOS: 38

<210> SEQ ID NO 1
<211> LENGTH: 847
<212> TYPE: DNA
<213> ORGANISM: Gibberella zeae

<400> SEQUENCE: 1
gggcccatgc cctggcgttg aagttctcgc tggaggggtt gagaggggag tttgcgtcgg      60
cagcgttgaa gaggtcggcg ctgctaccgg taaagtgatg cgaagtgttt gtgtagttgc     120
gggcgagatc tctaacgata gagtgtcgtc ggatcatctc ttcggtctgg gggccttcat     180
cttcgtcgtc tgaactcatc tggtcgcctg gggcggaagc ggcaggtttt tcggagtgag     240
gttgctcatt gccgacgatt gtgtcgtggc tgcgactgct ttgctctgag cgtgtcgagc     300
tcatgtttgc ctcggggagg gccattatgt ttgcgctgca agacagatat ctgtctgcgt     360
tgctagtagt ttgggttatt gtattaagta gataggtaaa ttaattaaac aagaacaaaa     420
gaaaggttca ggtaataaat agatcaatag taataatgaa tgaaagatga tatgatgcaa     480
```

```
aaataccgct ggcaggctgt tgcagcttct taatacaaag gtgccggata gatggtgatc      540
tccgtcgaac cgaaaggggt gtgggatgcg ggtcaccaac tcacggattc cgtcgacttc      600
ccgaccccga gtggatattg atcgggttca gtaggctacc cgaagtgata gtcgagagat      660
ttgcagtgta aagaggattg aagcaaatac tcgggtttgt cccgttactc ggattcccat      720
cttgccttcc aagaccgaga gacttgggac tgactatctt atcacgacat ttcttctttt      780
cgcttccaaa caaagcgttt tatgcagtca tcattgatcc agaccagaga gaacgaaagt      840
aaccatg                                                                847
```

```
<210> SEQ ID NO 2
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagagaacga aagtaaccat ggtgagcaag ggcgaggagc                             40
```

```
<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggcttggctg gagctagtgg agg                                               23
```

```
<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aacccgcggt cggcatctac tcta                                              24
```

```
<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatgtaggag ggcgtggata tgt                                               23
```

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaacccgctc gtctggctaa g                                                 21
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagcgtgtca cctaccgaga gc                                              22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
catgccctgg cgttgaagtt                                                 20

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctcgccctt gctcaccatg gttactttcg ttctctctgg                           40

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctccactag ctccagccaa gcctaatttg gcgttggttg gtctt                     45

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acgatcccgg tgcttggtt                                                  19

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tggttccgtg ccgtttgtga ta                                              22

<210> SEQ ID NO 13
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggcttctg atcagcaacg cc                                              22

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tcatgcctcc atcttctctc tttc                                            24

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tagagtagat gccgaccgcg ggttcatgcc ctggcgttga agtt                      44

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggttactttc gttctctctg gtct                                            24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcggtggtac gtaagtcggt ttct                                            24

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgtgctgccc gagtgaagtt t                                               21

<210> SEQ ID NO 19
<211> LENGTH: 43
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 19
tccactagct ccagccaagc cggtatggcg taattctgct tgg                      43

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gagagaacga aagtaaccat gtcagaaatc aacactacaa acgg                     44

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atggccgtcg ttgtggattt g                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acttggggtc ggcgtagatg c                                              21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgttgtcaag cgcacctcca ta                                             22

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgcgcgatc tcctcttgtt c                                              21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 25
atggcacccg aacaacaacg ac                                             22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctgatgcct ctcatcagga ctc                                            23

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tcgtcgtggg cttcatgttg taga                                           24

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggtcgatgt tgggcggtaa gt                                             22

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgcccttgct caccatggtt tgtgttatac gataagccac tagccg                   46

<210> SEQ ID NO 30
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctccactag ctccagccaa gccatgcgct tgctacgggg acag                     44

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 31
accaaaagac gatgagggtg ctatc                                       25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agcctctcct gaaattgcta aacga                                       25

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cctcagcggt gtagatagtt tctccc                                      26

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gtttctcccc tgtgatgctt gtgc                                        24

<210> SEQ ID NO 35
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
cgcccttgct caccatggtt tatgcttata cgatatgcgc actagc                46

<210> SEQ ID NO 36
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cctccactag ctccagccaa gccgggtatt gggttattgg ggagttcat             49

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
tccccagaat ttccccaaca atg                                              23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
taggtccagg ccgccatact g                                                21
```